(12) United States Patent
Malek

(10) Patent No.: US 6,652,832 B2
(45) Date of Patent: Nov. 25, 2003

(54) SYNTHESIS OF ZSM-12

(75) Inventor: Andrzej Mariusz Malek, Doylestown, PA (US)

(73) Assignee: ExxonMobil Oil Corporation, Fairfax, VA (US)

( * ) Notice: Subject to any disclaimer, the term of this patent is extended or adjusted under 35 U.S.C. 154(b) by 85 days.

(21) Appl. No.: 10/066,514

(22) Filed: Jan. 31, 2002

(65) Prior Publication Data
US 2002/0150533 A1 Oct. 17, 2002

Related U.S. Application Data
(60) Provisional application No. 60/266,527, filed on Feb. 5, 2001.

(51) Int. Cl.$^7$ .................................................. C01F 7/00
(52) U.S. Cl. ................. 423/706; 423/709; 423/DIG. 33
(58) Field of Search ................................. 423/760, 709, 423/DIG. 33

(56) References Cited
U.S. PATENT DOCUMENTS

| | | |
|---|---|---|
| 3,832,449 A | 8/1974 | Rosinski et al. |
| 4,391,785 A | 7/1983 | Rosinski et al. |
| 4,452,769 A | 6/1984 | Chu et al. |
| 4,537,758 A | 8/1985 | Chu et al. |
| 4,539,193 A | 9/1985 | Valyocsik |
| 4,552,738 A | 11/1985 | Rubin |
| 4,552,739 A | 11/1985 | Kühl |
| 4,585,637 A | 4/1986 | Rubin |
| 4,585,746 A | 4/1986 | Valyocsik ............. 502/62 |
| 4,954,325 A | 9/1990 | Rubin et al. |
| 4,981,663 A | 1/1991 | Rubin |
| 5,021,141 A | 6/1991 | Rubin ............. 208/46 |
| 5,187,132 A * | 2/1993 | Zones et al. |
| 5,192,521 A | 3/1993 | Moini et al. ............. 423/713 |

* cited by examiner

*Primary Examiner*—David Sample

(57) ABSTRACT

This invention provides a process for the synthesis of ZSM-12 using the N,N-dimethylhexamethyleneimine cation as a directing agent. The process enables ZSM-12 to be produced at silica/alumina molar ratios below 50 with little or no co-production of impurity phases. Small crystal forms of ZSM-12 can also be produced using the process of the invention.

9 Claims, 2 Drawing Sheets

SYNTHESIS OF ZSM-12

CROSS-REFERENCE TO RELATED APPLICATIONS

This application claims priority to application Ser. No. 60/266,527, filed Feb. 5, 2001, which is hereby incorporated by reference.

BACKGROUND OF THE INVENTION

1. Field of the Invention

This invention relates to a process for the synthesis of the porous crystalline material ZSM-12, to ZSM-12 produced by said process, and to use of the resultant ZSM-12 as a catalyst for organic compound, e.g., hydrocarbon compound, conversion.

More particularly, this invention relates to a process for synthesizing aluminosilicate ZSM-12 having a low silica to alumina molar ratio and substantially free of impurity phases.

2. Discussion of the Prior Art

ZSM-12 and its conventional preparation in the presence of a tetramethylammonium or tetraethylammonium directing agent are taught by U.S. Pat. No. 3,832,449, the entire disclosure of which is incorporated herein by reference. ZSM-12 has a distinctive X-ray diffraction pattern which distinguishes it from other known crystalline materials.

U.S. Pat. No. 4,391,785 discloses a method for the synthesis of ZSM-12 from a reaction mixture comprising, as a directing agent, a compound selected from the group consisting of a dimethyl pyridinium halide and a dimethyl pyrrolidinium halide.

U.S. Pat. Nos. 4,452,769 and 4,537,758 disclose methods for synthesizing ZSM-12 from a reaction mixture containing methyltriethylammonium ions as the directing agent.

Other organic directing agents that have been used to synthesize ZSM-12 include bis (dimethylpiperidinium) trimethylene ions (see U.S. Pat. No. 4,539,193), benzyltriethylammonium ions (see U.S. Pat. No. 4,552,738), dimethyldiethylammonium ions (see U.S. Pat. No. 4, 552,739), benzyltrimethylammonium ions (see U.S. Pat. No. 4,585,637), bis (N-methylpyridyl) ethylinium ions (see U.S. Pat. No. 4,5852,746) and bis (methylpyrrolidinium)-diquat-n, where n=4, 5 or 6 (see U.S. Pat. No. 5,192,521).

Hexamethyleneimine has been used as a directing agent to synthesize a variety of different crystalline structures, including MCM-22 (U.S. Pat. No. 4,954,325), MCM-35 (U.S. Pat. No. 4,981,663) and ZSM-12 (U.S. Pat. No. 5,021,141). In particular, the examples of U.S. Pat. No. 5,021,141 disclose the use of hexamethyleneimine to synthesize ZSM-12 with silica/alumina mole ratios varying between 62 and 852. ZSM-12 synthesized using hexamethyleneimine as the directing agent tends to crystallize as large hexagonal platelets having edge dimensions of about 2000 nm.

Existing methods for the synthesis of ZSM-12 suffer from the problem that they tend to produce impurity phases, such as ZSM-5, especially when at product silica/alumina molar ratios less than 100. According to the present invention, it has now been found that a novel directing agent, the N,N-dimethylhexamethyleneimine cation, can be used to synthesize ZSM-12 at silica/alumina molar ratios below 50 with little or no coproduction of impurity phases. In addition, ZSM-12 synthesized using the N,N-dimethylhexamethyleneimine cation as the directing agent tends to crystallize as small crystals with dimensions of about 50 nm.

It is to be appreciated that, although ZSM-12 is normally synthesized as an aluminosilicate, the framework aluminum can be partially or completely replaced by other trivalent elements, such as boron, iron and/or gallium, and the framework silicon can be partially or completely replaced by other tetravalent elements such as germanium.

SUMMARY OF THE INVENTION

According to the invention, there is provided a process for synthesizing the porous, crystalline material ZSM-12 which comprises the steps of:

(i) preparing a mixture capable of forming said material, said mixture comprising sources of alkali or alkaline earth metal (M), an oxide of trivalent element (X), an oxide of tetravalent element (Y), hydroxyl ($OH^-$) ions, water and N,N-dimethylhexamethyleneimine ions (R), wherein said mixture has a composition, in terms of mole ratios, within the following ranges:

| | |
|---|---|
| $YO_2/X_2O_3 =$ | at least 30 |
| $H_2O/YO_2 =$ | 30–70 |
| $OH^-/YO_2 =$ | 0.15–0.45 |
| $M/YO_2 =$ | 0.15–0.45 |
| $R/YO_2 =$ | 0.20–0.55, |

(ii) maintaining said mixture under sufficient conditions until crystals of said material are formed; and (iii) recovering said crystalline material from step (ii).

Preferably, said reaction mixture has a composition in terms of mole ratios within the following ranges:

| | |
|---|---|
| $YO_2/X_2O_3 =$ | 40–200 |
| $H_2O/YO_2 =$ | 35–45 |
| $OH^-/YO_2 =$ | 0.30–0.40 |
| $M/YO_2 =$ | 0.20–0.40 |
| $R/YO_2 =$ | 0.30–0.45. |

Preferably, M is sodium.

Preferably, said mixture also contains a source of tetraethylammonium ions.

DETAILED DESCRIPTION OF THE INVENTION

Figure 1:
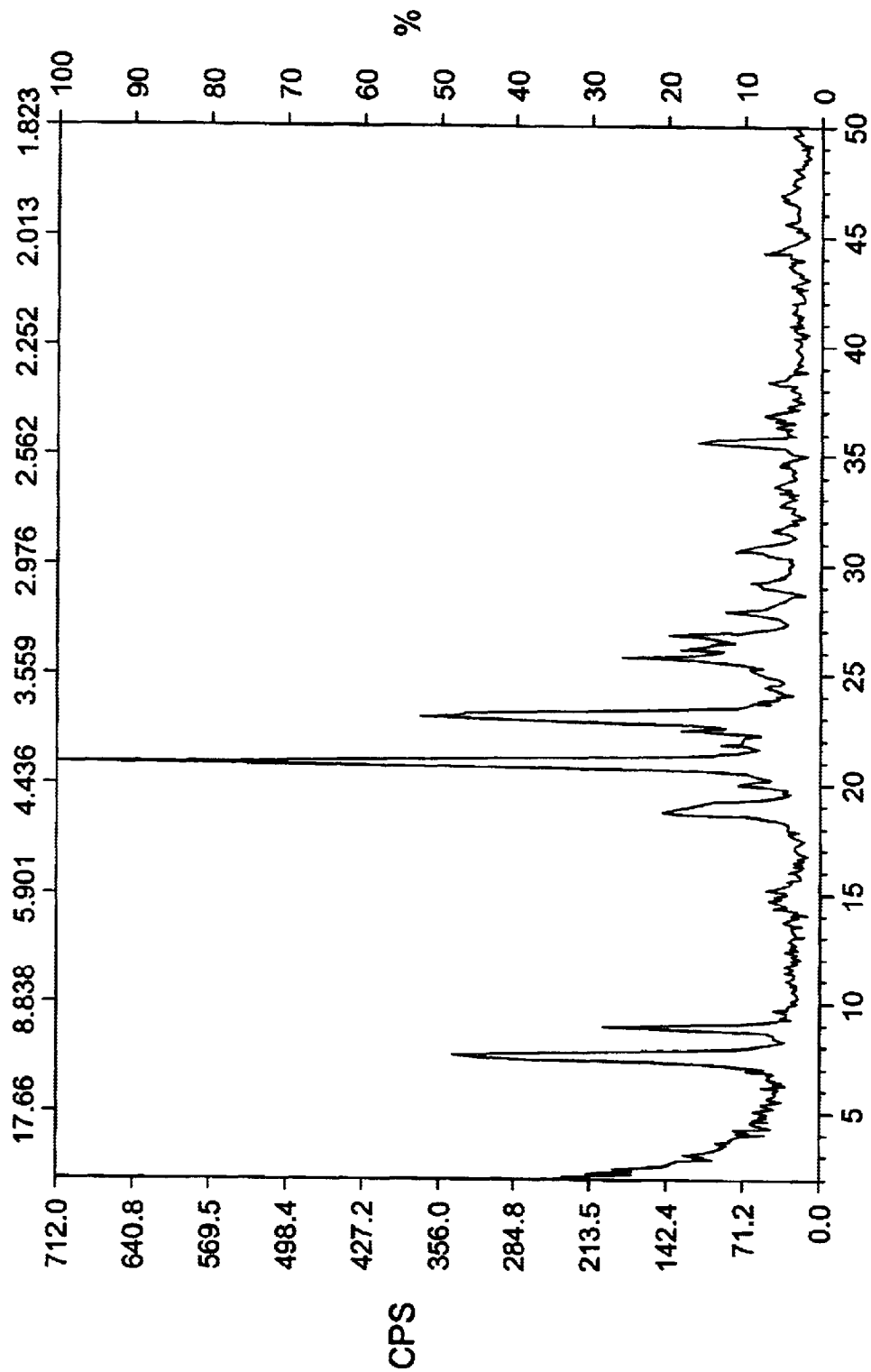
FIG. 1 shows the X-ray diffraction pattern of the as-synthesized product of Example 1.

The ZSM-12 produced by the process of the invention has an X-ray diffraction pattern, characterized by the X-ray diffraction lines in Table 1 below:

TABLE 1

| D-spacing (Å) | Relative Intensity [100 × I/Io] |
|---|---|
| 11.9 ± 0.2 | m |
| 10.1 ± 0.2 | m |
| 4.76 ± 0.1 | w |
| 4.29 ± 0.08 | vs |
| 3.98 ± 0.08 | m |
| 3.87 ± 0.07 | vs |

TABLE 1-continued

| D-spacing (Å) | Relative Intensity [100 × I/Io] |
|---|---|
| 3.49 ± 0.07 | w |
| 3.38 ± 0.07 | m |
| 3.20 ± 0.06 | w |
| 3.05 ± 0.05 | w |
| 2.54 ± 0.03 | w |

These X-ray diffraction data were collected with a Scintag diffractometer using copper K-alpha radiation. The diffraction data were recorded by step-scanning at 0.02 degrees of two-theta, where theta is the Bragg angle, and a counting time of 1 second for each step. The interplanar spacings, d's, were calculated in Angstrom units (A), and the relative intensities of the lines, I/Io, where Io is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (75–100), s=strong (50–74), m=medium (25–49) and w=weak (0–24). It should be understood that diffraction data listed for this sample as single lines may consist of multiple overlapping lines which under certain conditions, such as differences in crystallite sizes or very high experimental resolution or crystallographic change, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history.

The crystalline material ZSM-12 prepared hereby has a composition involving the molar relationship:

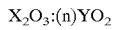

wherein X is a trivalent element, such as aluminum, boron, iron, indium and/or gallium, preferably aluminum; Y is a tetravalent element, such as silicon, tin and/or germanium, preferably silicon; and n is at least 30 and more usually from about 40 to about 200. In the as-synthesized form, the crystalline material prepared hereby has a formula, on an anhydrous basis and in terms of moles of oxides per n moles of $YO_2$, as follows:

wherein M is an alkaline or alkaline earth metal, R is the N,N-dimethylhexamethyleneimine cation and TMA is the tetramethylammonium cation. The M, TMA and R components are associated with the material as a result of their presence during crystallization, and are easily removed by post-crystallization methods hereinafter more particularly described.

The particular effectiveness of the presently required organic directing agent, the N,N-dimethylhexamethyleneimine cation, as compared with other directing agents, for the present synthesis is in its ability to produce ZSM-12 with a silica/alumina molar ratio below 100, and more preferably below 50 with little or no coproduction of impurity phases. In view of its increased aluminum content, it is believed that the ZSM-12 produced by the process of the invention will have an enhanced activity when used as an acid catalyst in reactions such as hydrocarbon conversion.

The ZSM-12 produced by the present process also tends to have smaller crystal size than that produced by conventional methods and hence should exhibit reduced mass transfer limitations.

The process of the invention involves initially producing a synthesis mixture containing sources of alkali or alkaline earth metal (M) cations, normally sodium, an oxide of a trivalent element (X), normally alumina, an oxide of a tetravalent element (Y), normally silica, N,N-dimethylhexamethyleneimine ions (R), normally present as the iodide salt, hydroxyl ions and water. The synthesis mixture has a composition, expressed in terms of mole ratios of oxides, as follows:

| Component | Useful | Preferred |
|---|---|---|
| $YO_2/X_2O_3$ | At least 30 | 40–200 |
| $H_2O/YO_2$ | 30–70 | 35–45 |
| $OH^-/YO_2$ | 0.20–0.45 | 0.30–0.40 |
| $R/YO_2$ | 0.20–0.55 | 0.30–0.45 |
| $M/YO_2$ | 0.15–0.45 | 0.20–0.40 |

The N,N-dimethylhexamethyleneimine iodide directing agent is conveniently prepared from commercially available hexamethyleneimine (HMI) by reacting 1 mol of HMI with 3 moles of methyl iodide in 300 ml of chloroform. First a solution of HMI in chloroform is prepared and methyl iodide is added gradually over 30 minutes. The mixture is refluxed overnight. The product is precipitated with 500 ml of THF filtered and dried at room temperature. The dried product is re-dissolved in 80 ml of chloroform and precipitated with 100 ml THF, filtered and dried at room temperature.

The ZSM-12 synthesis mixture may also contain tetramethylammonium ions, normally the hydroxide (TMAOH), such that the $TMA/YO_2$ molar ratio is from about 0 to about 0.3.

The synthesis method of the invention functions with or without added nucleating seeds. In a preferred embodiment, the reaction mixture contains 0.05–5 wt % nucleating seeds of ZSM-12.

Crystallization is carried out under either stirred or static conditions at a temperature of 130 to 200° C., preferably 150 to 175° C., for 48 hours to 14 days and the resultant crystals are separated from the mother liquor and recovered.

When the only organic medium present in the synthesis mixture is N,N-dimethylhexamethyleneimine, the ZSM-12 produced by the process of the invention tends to be in the form of small crystals with a diameter of about 50 nm aggregated into irregular clusters with cross sectional dimensions of about 200

ZSM-12 synthesized by the process of the invention contains the organic material(s) used as the directing agent and, prior to use as a catalyst or adsorbent, the as-synthesized material is normally treated to remove part or all of the organic constituent. This is conveniently effected by heating the as-synthesized material at a temperature of from about 250° C. to about 550° C. for from 1 hour to about 48 hours.

To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB and VIII of the Periodic Table of the Elements.

The crystalline material of this invention, when employed either as an adsorbent or as a catalyst in an organic compound conversion process should be dehydrated, at least partially. This can be done by heating to a temperature in the range of 200° C. to about 370° C. in an atmosphere such as air or nitrogen, and at atmospheric, subatmospheric or superatmospheric pressures for between 30 minutes and 48 hours. Dehydration can also be performed at room temperature merely by placing the ZSM-12 in a vacuum, but a longer time is required to obtain a sufficient amount of dehydration.

Synthetic ZSM-12 crystals prepared in accordance herewith can be used either in the as-synthesized form, the hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to the ZSM-12 such as, for example, by, in the case of platinum, treating the material with a platinum metal-containing ion. Suitable platinum compounds for this purpose include chloroplatinic acid, platinous chloride and various compounds containing the platinum amine complex. Combinations of metals and methods for their introduction can also be used.

When used as a catalyst, it may be desirable to incorporate the ZSM-12 prepared hereby with another material resistant to the temperatures and other conditions employed in certain organic conversion processes. Such matrix materials include active and inactive materials and synthetic or naturally occurring zeolites as well as inorganic materials such as clays, silica and/or metal oxides, e.g. alumina, titania and/or zirconia. The latter may be either naturally occurring or in the form of gelatinous precipitates, sols or gels including mixtures of silica and metal oxides. Use of a material in conjunction with the ZSM-12, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline catalytic materials have been incorporated into naturally occurring clays, e.g. bentonite and kaolin. These materials, i.e. clays, oxides, etc., function, in part, as binders for the catalyst. It is desirable to provide a catalyst having good crush strength because in a petroleum refinery the catalyst is often subjected to rough handling, which tends to break the catalyst down into powder-like materials which cause problems in processing.

Naturally occurring clays which can be composited with the hereby synthesized crystalline material include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the present crystals can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline material and matrix vary widely with the crystalline material content ranging from about 1 to about 90 percent by weight, and more usually in the range of about 2 to about 50 percent by weight of the composite.

Aluminosilicate ZSM-12 produced by the process of the invention is useful as a catalyst in organic compound, and in particular hydrocarbon, conversion reactions where high activity is important. In particular, when combined with a hydrogenation component, such as platinum, palladium or rhenium, the ZSM-12 is useful in transalkylation of toluene with heavier, $C_9+$, alkylaromatics and the dealkylation of ethyl- and propyl-aromatics, such as ethylbenzene.

In order to more fully illustrate the nature of the invention and the manner of practicing same, the following examples are presented.

EXAMPLE 1

A gel having the following molar composition was prepared from distilled water, silica (HiSil 233), a 50 wt % aqueous sodium hydroxide solution, sodium aluminate and N,N-dimethylhexamethyleneimine iodide (R):

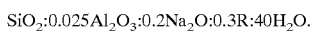

$SiO_2:0.025Al_2O_3:0.2Na_2O:0.3R:40H_2O$.

Zeolite crystallization was conducted by heating the gel under autogenous pressure at 150° C. for 168 hours without stirring. The resultant zeolite product was filtered, washed and dried. X-ray analysis was conducted on the dried, as-synthesized product with a Scintag diffractometer using copper K-alpha radiation and with the diffraction data being recorded by step-scanning at 0.05 degrees of two-theta and a counting time of 1 second for each step. The X-ray pattern indicated the product to be ZSM-12 without visible impurity phases (FIG. 1), although the X-ray lines showed evidence of broadening suggesting a small crystallite size. This was confirmed by scanning electron microscopy which showed the ZSM-12 product to be in the form of irregular aggregates, around 200 nm in diameter, of small crystallites having an aspect ratio of nearly 1 and a diameter of 50 mm or less.

Elemental analysis of the crystalline product of Example 1 indicated a silica/alumina molar ratio of 39.

EXAMPLE 2

A gel having the following molar composition was prepared from distilled water, silica (HiSil 233), a 50 wt % aqueous sodium hydroxide solution, sodium aluminate, tetramethylammonium hydroxide (TMAOH) and N,N-dimethylhexamethyleneimine iodide (R):

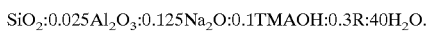

$SiO_2:0.025Al_2O_3:0.125Na_2O:0.1TMAOH:0.3R:40H_2O$.

Figure 2:
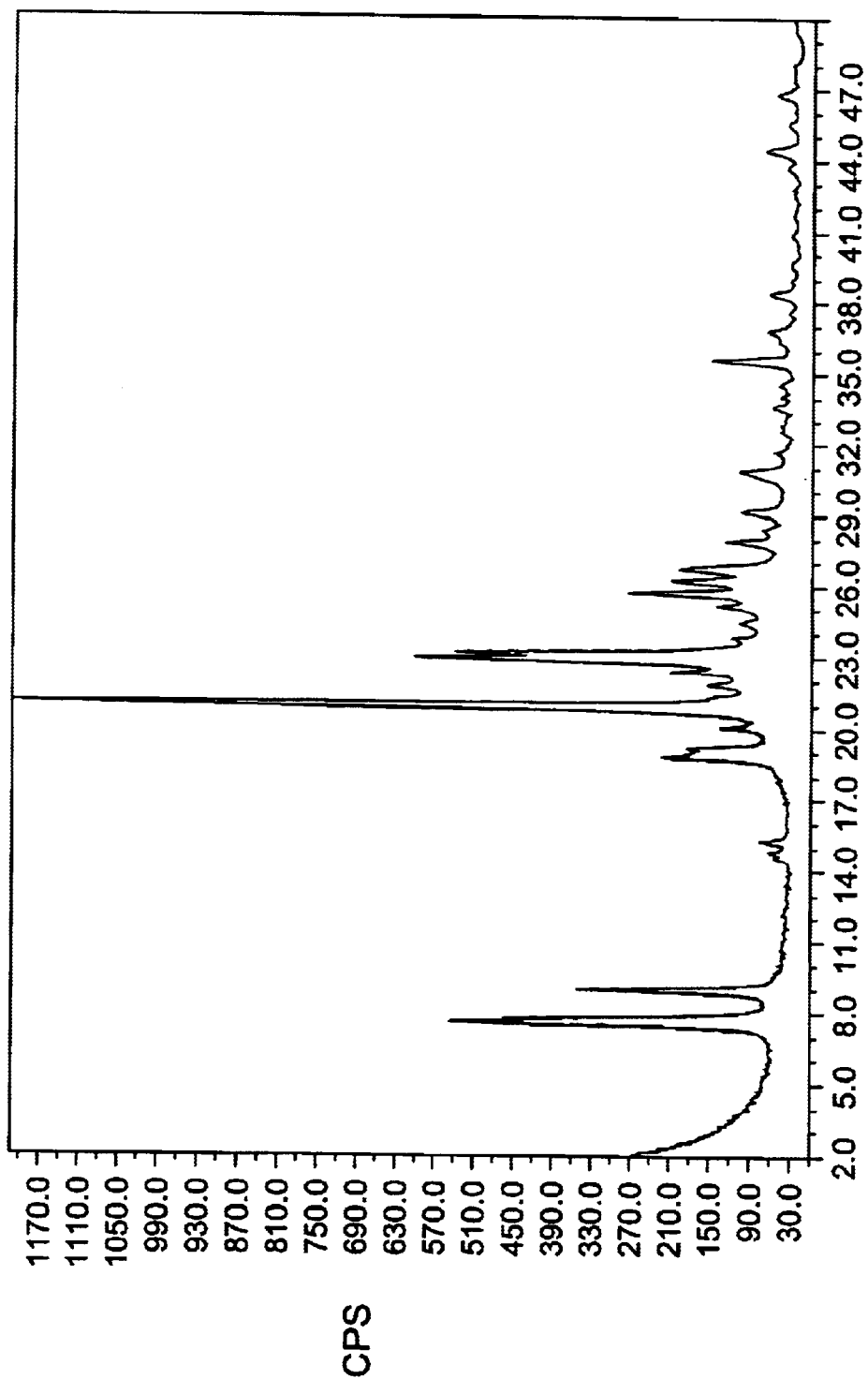
FIG. 2 shows the X-ray diffraction pattern of the as-synthesized product of Example 2.

Zeolite crystallization was conducted as in Example 1 and the resultant zeolite product was filtered, washed and dried. X-ray analysis was conducted on the dried, as-synthesized product with a Scintag diffractometer using copper K-alpha radiation and with the diffraction data being recorded by step-scanning at 0.02 degrees of two-theta and a counting time of 10 seconds for each step. The X-ray pattern showed the product to be ZSM-12 without visible impurity phases (FIG. 2).

What is claimed is:

1. A process for synthesizing the crystalline material ZSM-12 which comprises the steps of:

(i) preparing a mixture capable of forming said material, said mixture comprising sources of alkali or alkaline earth metal (M), an oxide of trivalent element (X), an oxide of tetravalent element (Y), hydroxyl (OH⁻) ions, water and N,N-dimethylhexamethyleneimine cations (R), wherein said mixture has a composition, in terms of mole ratios, within the following ranges:

| | |
|---|---|
| $YO_2/X_2O_3 =$ | at least 30 |
| $H_2O/YO_2 =$ | 30–70 |
| $OH^-/YO_2 =$ | 0.15–0.45 |
| $M/YO_2 =$ | 0.15–0.45 |
| $R/YO_2 =$ | 0.20–0.55, |

(ii) maintaining said mixture under sufficient conditions until crystals of said material are formed; and (iii) recovering said crystalline material from step (ii).

2. The process of claim 1, wherein said reaction mixture has a composition in terms of mole ratios within the following ranges:

| | |
|---|---|
| $YO_2/X_2O_3 =$ | 40–200 |
| $H_2O/YO_2 =$ | 35–45 |
| $OH^-/YO_2 =$ | 0.30–0.40 |
| $M/YO_2 =$ | 0.20–0.40 |
| $R/YO_2 =$ | 0.30–0.45. |

3. The process of claim 1, wherein M is sodium.

4. The process of claim 1, wherein said mixture also contains a source of tetramethylammonium cations.

5. The process of claim 1, wherein said mixture further comprises seed crystals in sufficient amount to enhance synthesis of said crystalline material.

6. The process of claim 5, wherein said seed crystals have the structure of ZSM-12.

7. The process of claim 1, wherein X is selected from the group consisting of aluminum, boron, iron, gallium, indium and mixtures thereof, and said Y is selected from the group consisting of silicon, germanium, tin and mixtures thereof.

8. The process of claim 1, wherein X comprises aluminum and Y comprises silicon.

9. ZSM-12 synthesized by the process of claim 1.

* * * * *